United States Patent [19]

Prossel et al.

[11] Patent Number: 5,925,775
[45] Date of Patent: Jul. 20, 1999

[54] AMIDOPROPYL-N-ALKYL-POLYLHYDROXYALKYLAMINE COMPOUNDS, PROCESSES FOR THEIR PREPARATION AND THEIR USE

[75] Inventors: Günter Prossel; Reinhard Vybiral, both of Burgkirchen; Werner Skrypzak, Hofheim; Hans Jürgen Scholz, Alzenau, all of Germany

[73] Assignee: Clariant GmbH, Frankfurt, Germany

[21] Appl. No.: 08/691,469

[22] Filed: Aug. 2, 1996

[30] Foreign Application Priority Data

Aug. 14, 1995 [DE] Germany ............... 195 29 810

[51] Int. Cl.$^6$ .................................. C07C 233/00
[52] U.S. Cl. .................. 554/55; 554/52; 554/68; 554/69; 564/157; 510/119; 510/123; 510/126; 510/130; 424/71
[58] Field of Search ................ 554/52, 69, 68, 554/55; 424/71; 564/157; 520/119, 123, 126, 130

[56] References Cited

U.S. PATENT DOCUMENTS 5,117,058  5/1992  Baker .
5,288,484  2/1994  Tashjian .

FOREIGN PATENT DOCUMENTS 9526210  12/1995  Australia .
4238211   1/1994  Germany .
4238207   5/1994  Germany .
95 32942 12/1995  WIPO .

*Primary Examiner*—Gary Geist
*Assistant Examiner*—Deborah D Carr
*Attorney, Agent, or Firm*—Miles B. Dearth

[57] ABSTRACT

Amidopropyl-N-alkyl-polyhydroxyalkylamines of the following formula (1)

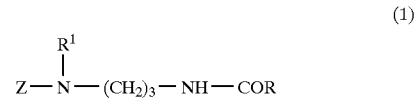

(1)

in which Z is a linear polyhydroxyhydrocarbon radical having at least 2 free or oxyalkylated hydroxyl groups, $R^1$ is a $C_1$ to $C_7$-alkyl radical or $C_2$ to $C_4$-hydroxyalkyl radical and COR is an aliphatic acyl radical having 6 to 22 carbon atoms, and salts thereof from an inorganic or organic acid are described. They are prepared by a) reaction of a compound of the formula (2)

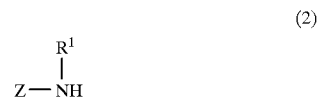

(2)

with acrylonitrile to give the compound of the formula (3)

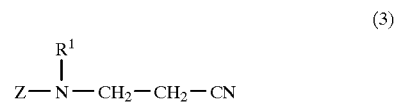

(3)

b) hydrogenation of the product obtained in step a) to give the compound of the formula (4)

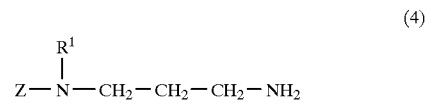

(4)

and c) monoacylation of the product obtained in step b) in the melt to give the compound of the formula (1) mentioned. The compounds according to the invention are readily soluble in water and water/alcohol mixtures and are advantageous co-surfactants for use in detergents and cleaning compositions and in cosmetic preparations for cleansing the hair and skin.

17 Claims, No Drawings

AMIDOPROPYL-N-ALKYL-POLYLHYDROXYALKYLAMINE COMPOUNDS, PROCESSES FOR THEIR PREPARATION AND THEIR USE

DESCRIPTION

DE-A-42 38 207 and DE-C-42 38 211 describe quaternized fatty acid polyhydroxyalkylamides which are derived formally from propylenediamines. These cationic surfactants are said to have a high water-solubility and be processable to highly concentrated, low-viscosity solutions or dispersions.

A novel class of polyhydroxyalkylamide compounds has now been found. These are amidopropyl-N-alkyl-polyhydroxyalkylamines and salts thereof with inorganic or organic acids.

The amidopropyl-N-alkyl-polyhydroxyalkylamines according to the invention correspond to the following formula (1)

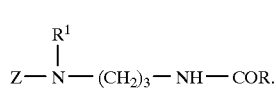

(1)

In this formula

Z is a linear polyhydroxyhydrocarbon radical having at least 2 free or oxyalkylated hydroxyl groups, $R^1$ is a $C_1$ to $C_7$-alkyl radical or $C_2$ to $C_4$-hydroxyalkyl radical and COR is an aliphatic acyl radical having 6 to 22 carbon atoms.

Preferred compounds of the formula (1) according to the invention are those in which Z is a polyhydroxyalkyl radical having 3 to 18 carbon atoms and 2 to 13 hydroxyl groups, and is preferably a radical of a sugar-alcohol which is derived from a reducing mono- or disaccharide, in particular from glucose, $R^1$ is methyl, ethyl, propyl, isopropyl or —$CH_2CH_2OH$ and COR is a fatty acyl radical having 8 to 18 carbon atoms.

The following may also be stated regarding COR and Z: the aliphatic acyl radical COR, which is preferably the fatty acyl radical mentioned, can be saturated or unsaturated (preferably mono- to triunsaturated). Examples which may be mentioned are the acyl radicals of caprylic, capric, lauric, palmitic, stearic and oleic acid, as well as coconut-acyl, tallow-acyl, preferably hydrogenated tallow-acyl, and the like. The fatty acid radical is often a mixture of two or more acyl groups, for example $C_{12}$ and $C_{14}$-acyl ($C_{12/14}$), $C_{16}$ and $C_{18}$-acyl ($C_{16/18}$) or $C_{12}$ to $C_{18}$-acyl. As already mentioned above, the linear polyhydroxyhydrocarbon radical preferably originates from sugar-alcohols derived from the group consisting of reducing sugars or reducing sugar derivatives. Preferred reducing sugars are the monosaccharides, preferably pentoses and hexoses, and the oligosaccharides, preferably disaccharides and, where appropriate, also trisaccharides. Examples of monosaccharides are glucose, galactose, mannose and talose as hexoses, and arabinose, ribose and xylose as pentoses. Of the monosaccharides, the hexoses are preferred. Examples of oligosaccharides (polysaccharides) are lactose, maltose, maltotriose and the like. Particularly preferred polyhydroxyalkyl radicals originate from reducing hexoses, in particular from glucose (sorbityl radical).

The salts, according to the invention, of a polyhydroxyalkylamine of the formula (1) with an inorganic or organic acid are in general derived from a mineral acid or from an aliphatic or aromatic carboxylic acid or hydroxycarboxylic acid. Preferred inorganic acids are hydrogen halide acids, such as HCl or HBr, carbonic acid, phosphoric acid or sulfuric acid. Preferred organic acids are $C_1$ to $C_3$-monocarboxylic acids, such as formic acid, acetic acid or propionic acid; $C_{12}$ to $C_{18}$-monocarboxylic acids, such as dodecanoic acid, palmitic acid, stearic acid or oleic acid; dicarboxylic acids of the formula HOOC—$(CH_2)_n$—COOH, in which n is 0 or an integer from 1 to 8, such as oxalic, malonic, succinic, glutaric or adipic acid and the unsaturated dicarboxylic acids fumaric and maleic acid; monohydroxy-monocarboxylic acids, such as glycolic acid (hydroxy-acetic acid) or lactic acid (α-hydroxy-propionic acid); monohydroxy-dicarboxylic acids, such as tartronic acid (monohydroxy-malonic acid) or malic acid (monohydroxy-succinic acid); dihydroxy-dicarboxylic acids, such as tartaric acid (dihydroxy-succinic acid); monohydroxy-tricarboxylic acids, such as citric acid (hydroxy-tricarballylic acid); hydroxy-benzoic acids, such as salicylic acid or gallic acid; and aromatic dicarboxylic acids (phthalic acids), such as o-phthalic acid or p-phthalic acid. Of the organic acids mentioned as anion-forming agents, the $C_1$ to $C_3$-mono-carboxylic acids, lactic acid and the fruit acids are particularly preferred.

In their formulae, the salts correspond to the following formula (1a)

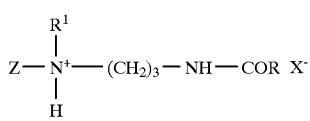

(1a)

in which Z, $R^1$ and COR have the meanings given and $X^-$ is an anion of an inorganic or organic acid.

In the case where $X^-$ is the anion of a polybasic inorganic or organic acid, the corresponding acid salts can also be partly or completely neutralized with the equivalent amount of inorganic or organic basic substances. However, the acid salt can also be partly or completely neutralized with the corresponding equivalent amount of an amidopropyl-N-alkyl-polyhydroxyalkylamine or N-alkyl-polyhydroxyalkylamine compound.

On the basis of the acids mentioned, a few examples of $X^-$ may be mentioned for further illustration: $Cl^-$, $Br^-$, $(SO_4^{2-})_{1/2}$, $(PO_4^{3-})_{1/3}$, $CH_3COO^-$, $C_{11}H_{23}COO^-$, $CH_3$—CH(OH)—$COO^-$ (anion of lactic acid), HOOC—CH(OH)—$CH_2$—$COO^-$ (anion of malic acid), $C_6H_5$—$COO^-$ (anion of benzoic acid) and the like.

The amidopropyl-N-alkyl-polyhydroxyalkylamines of the formula (1) according to the invention are prepared by a) reaction of a compound of the formula (2)

(2)

in which Z and $R^1$ have the meanings given, with acrylonitrile ($CH_2$=CH—CN) in a polar solvent at a temperature of 50 to 100° C. to form a compound of the formula (3)

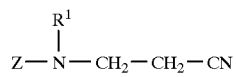

(3)

in which Z and R¹ have the meanings given, b) reaction of the product obtained in step a) with hydrogen in the presence of ammonia and a hydrogenation catalyst at a temperature of 20 to 80° C. under a hydrogen pressure of 10 to 80 bar, to form a compound of the formula (4)

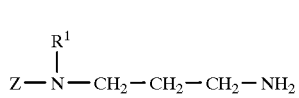

(4)

in which Z and R¹ have the meanings given, and c) monoacylation of the product obtained in step b) with an acid or acid derivative derived from the acyl radical COR in formula (1) in the melt in the presence of an alkaline catalyst at a temperature of 80 to 130° C. to form a compound of the formula (1) mentioned.

The process according to the invention thus comprises a combination of several specific reactions. Preferred embodiments of the individual process stages are described below.

The acrylonitrile addition in step a) is carried out in the presence of a polar solvent at a temperature of preferably 60 to 90° C. The reaction component which is a compound of the formula (2), for example N-methylglucamine (commercially obtainable), and acrylonitrile are preferably employed in a molar ratio of about 1:1. Suitable polar solvents are $C_1$ to $C_4$-alkanols, such as methanol, ethanol, propanol or isopropanol, $C_2$ to $C_4$-diols, such as monoethylene glycol, diethylene glycol, monopropylene glycol or dipropylene glycol, and the mono- or diethers of these diols, such as monoethylene glycol monomethyl ether and the like. It is also possible to employ a mixture of the liquids mentioned. Preferred solvents are methanol, ethanol or isopropanol. The solvent is employed in an amount such that a reaction mixture which is preferably 10 to 50% strength by weight is present. The reaction is in general carried out under atmospheric pressure or under the system pressure which is established, and proceeds quantitatively over a reaction time of about 1 to 3 hours. The resulting product essentially comprises a compound of the formula (3) mentioned and the solvent employed. Removal of the solvent and isolation of the compound as such is not necessary for the further reaction.

In step b), the solution obtained in step a) is reacted with hydrogen at a temperature of preferably 30 to 60° C. under a pressure of preferably 30 to 60 bar for conversion of —CN into —$CH_2NH_2$. About 2 mol of hydrogen are required per mole of compound of the formula (3). The reaction is carried out in the presence of ammonia and a hydrogenation catalyst. The amount of ammonia for reducing formations of by-products is in general 1 to 10 mol, preferably 3 to 6 mol, per mole of nitrile compound of the formula (3). The customary hydrogenation catalysts, such as cobalt, copper, iron, nickel, palladium and/or platinum, can be employed, nickel catalysts being preferred. The metallic hydrogenation catalyst can be employed as a supported catalyst, a powdered catalyst or as a Raney catalyst. Raney nickel is preferred. The hydrogenation catalyst is in general employed in an amount of 0.05 to 5% by weight, preferably in an amount of 0.1 to 2% by weight, based on the nitrile compound to be hydrogenated (the percentages by weight mentioned relate to the metal alone, i.e. do not also include, for example, the support material). The hydrogenation to give the compound of the formula (4) proceeds practically quantitatively over a reaction time of about 2 to 6 hours. The resulting product thus essentially comprises a compound of the formula (4) and the solvent employed in step a).

Since the further reaction (acylation) is to be carried out in the melt, i.e. in the absence of any solvent, the compound of the formula (4) is isolated from the solution obtained in step b). This can be effected, for example, by distilling off the solvent at a temperature of preferably 40 to 60° C., if appropriate applying a vacuum of about 10 to 50 mbar (waterpump vacuum), after the hydrogenation catalyst has first been filtered off.

In step c) of the process according to the invention, the compound of the formula (4) obtained in step b) is monoacylated (amidated) in the melt at a temperature of preferably 90 to 120° C. in the presence of a basic catalyst. The acylating agent, which is in general employed in an amount of 1 to 1.1 mol, preferably 1.01 to 1.05 mol, per mole of compound of the formula (4), is preferably a fatty acid or a fatty acid derivative, such as a fatty acid halide or fatty acid $C_1$ to $C_4$-alkyl ester, derived from the acyl radical COR in formula (1). The preferred acylating agent is a fatty acid $C_1$ to $C_4$-alkyl ester, a fatty acid methyl ester being particularly preferred. The basic acylation catalyst is preferably an alkali metal hydroxide, such as sodium hydroxide or potassium hydroxide, or an alkali metal $C_1$ to $C_4$-alcoholate, such as sodium methylate. The amount of basic catalyst is 0.01 to 0.2 mol, preferably 0.05 to 0.1 mol, per mole of compound of the formula (4). The acylation is carried out under atmospheric pressure or, preferably, by applying a vacuum, in which case faster removal of the volatile contents formed, such as, for example, methanol, is achieved. The vacuum is in general 5 to 100 mbar, preferably 10 to 50 mbar. It has proved to be advantageous to carry out the acylation (amidation) in a manner such that a mixture of the amine compound of the formula (4) and the basic catalyst compound is first prepared and this (solvent-free) mixture is acylated in the melt as described above. The product obtained in step c) essentially comprises the desired compound of the formula (1). The compounds of the formula (1) described are thus obtained in a high yield and in a high purity by the process according to the invention.

The salts according to the invention are prepared by bringing the amidoamines of the formula (1) according to the invention together with an inorganic or organic acid. Suitable and preferred acids are mentioned specifically above. In general, an approximately 10 to 40% strength by weight aqueous or aqueous/alcoholic solution of the acid is prepared and the pulverulent amidoamine is stirred into this solution, as a rule at room temperature (about 20 to 30° C.). Suitable alcohols are the $C_1$ to $C_3$-alkanols, such as methanol, ethanol, propanol and/or isopropanol. The aqueous or aqueous/alcoholic solutions of the salts according to the invention essentially comprise 10 to 60% by weight, preferably 15 to 40% by weight, of salt compound and water or water/alcohol as the remainder to make up 100% by weight. Since the aqueous or aqueous/alcoholic solutions often can already be employed as such, isolation of the salt compound from the solution is not necessary.

The amidopropyl-N-alkyl-polyhydroxyalkylamine compounds according to the invention are valuable surface-active compounds which can be employed in many instances. Thus, for example, they can be employed as such or as a mixture with anionic, cationic and/or nonionic surfactants as detergents and cleaning compositions, hair and body cleansing compositions, textile treatment compositions and the like, and in particular in the form of solid products, solutions, dispersions, emulsions, pastes and the like. In particular, the salts can be employed as co-surfactants in detergents and cleaning compositions as well as hair and body cleansing preparations, as foams and for foam stabilization. Since these amidoamines are readily biologically degradable and can be prepared from raw materials which regenerate, they have recently acquired greater importance.

The salts of these amidopropyl-N-alkyl-polyhydroxyalkylamines are very readily soluble in water and mixtures of water and $C_1$ to $C_3$-alcohols. They have, as an advantageous property, a good skin and mucosa tolerance, as in vitro tests (red blood cell test, zein test) show, which means that the skin tolerance of the formulations prepared therefrom is noticeably improved. Furthermore, the compounds according to the invention, specifically the salts of lauryl/myristylamidopropyl-N-methylglucamine, show an excellent foaming power and a foam-stabilizing action. In combination with the base surfactants usually used (for example sodium alkyl ethersulfates), a potent viscosity-increasing action is obtained.

The following examples are intended to illustrate the subject matter of the invention in more detail, without limiting it thereto. Unless stated otherwise, all the parts and percentages are based on the weight.

I. PREPARATION EXAMPLES

Example 1

(first process stage) N-Methyl-N-(β-cyanoethyl)-glucamine 607 g (3.1 mol) of N-methylglucamine (NMG) are suspended in 729 g of methanol in a 2 l four-necked flask with a stirrer, dropping funnel, reflux condenser and thermometer. The reaction mixture is heated to 63° C., while stirring. 163 g (3.1 mol) of acrylonitrile are added dropwise in the course of 30 minutes. When the addition has ended, the clear solution is stirred at 63° C. for a further 3 hours. According to analysis by gas chromatography, the conversion in the reaction is complete, so that the reaction product can be employed directly for the hydrogenation (second process stage).

Example 2

(second process stage, hydrogenation) N-Methyl-N-(γ-aminopropyl)-glucamine (MAPG)

1500 g of N-methyl-N-(γ-cyanoethyl)-glucamine (51.4% strength in methanol, 3.1 mol of educt) from Example 1 and 111 g of Raney nickel (water-moist, about 70% pure) are introduced into a 2 l stirred autoclave. After the autoclave has been closed, it is flushed with nitrogen and hydrogen and let down again. 330 ml of liquefied ammonia gas and then 50 bar of hydrogen are subsequently forced in. Hydrogenation is carried out under 40 to 50 bar at a temperature of 25 to 45° C., while stirring, until no further hydrogen is taken up (about 3 hours). The catalyst is filtered off at 40° C. over a pressure filter press, while the system is simultaneously let down. The methanolic solution of the hydrogenated product is concentrated on a rotary evaporator at 70° C. under a waterpump vacuum. 742 g of N-methyl-N-(γ-aminopropyl)-glucamine—corresponding to a yield of 95% of theory—are obtained in the form of a colorless powder.

Melting point: 106° C.
Composition ($^{13}$C—NMR): 96 mol % of MAPG 2 mol % of NMG 2 mol % of di-NMG Alternatively to the hydrogenation described, the procedure can also be as follows: when the hydrogenation operation has ended, the catalyst is allowed to settle in the course of 1 hour and the supernatant solution is forced over the pressure filter press in order to filter off small amounts of catalyst residues. Further working up is carried out as is described in Example 2. For subsequent batches, without further addition of catalyst, a series of at least 12 subsequent batches can be operated in this manner by pumping in the reactants in each case (after each emptying of the autoclave), without the catalyst activity being exhausted and with a constant quality of the end product.

Example 3

(amidation) Lauryl/myristylamidopropyl-N-methylglucamine (LAP-NMG)

300 g (1.1 mol) of MAPG from Example 2 are melted at 100° C. in a 2 l four-necked flask with a stirrer, dropping funnel, distillation attachment and thermometer. 4.5 g (0.056 mol) of 50% strength sodium hydroxide solution are added and the mixture is heated to 130° C. After 15 minutes at 130° C. under atmospheric pressure and 15 minutes under a vacuum of 16 mbar, all of the water is distilled off. 242 g (1.1 mol) of methyl laurate/myristate are added dropwise at 100° C. in the course of 20 minutes. The methanol formed is distilled off at 100° C. under a vacuum of 16 bar in the course of 4 hours. 508 g of a pale amber-colored mass which solidifies on cooling are obtained in a virtually quantitative yield. After commutation in a mixer, a colorless powder which has a melting range from 93 to 99° C. and, according to $^{13}$C-NMR spectroscopy, comprises 96% pure LAP-NMG is formed.

Example 4

(Amidation) Palmityl/stearylamidopropyl-N-methylglucamine (PAP-NMG)

572 g of PAP-NMG are obtained in a practically quantitative yield with a purity of 94 mol % ($^{13}$C-NMR) in a manner corresponding to that described in Example 3 from 300 g (1.1 mol) of MAPG from Example 2 by reaction with methyl palmitate/stearate (after addition of the catalyst and treatment as described) at 120° C. after a reaction time of 4 hours under a vacuum of 16 bar. After commutation of the melt, a colorless powder having a melting range from 101 to 104.5° C. is formed.

TABLE 1

[Composition of the end products ($^{13}$C-NMR)]

| Example | 3 | 4 |
|---|---|---|
| Fatty alkyl-amidopropyl-NMG | 96 mol % | 94 mol % |
| di-NMG-amine | 2 mol % | 2 mol % |
| N-methylglucamine | 2 mol % | 2 mol % |
| Ester-amide | — | 2 mol % |

Example 5

Lauryl/myristyltylamidopropyl-N-methylglucamine hydrochloride (LAP-NMG.HCl) solution 900 ml of water are initially introduced into a 2 l three-necked flask with a stirrer, reflux condenser and thermometer, 17.9 g of concentrated hydrochloric acid (37% strength, 0.182 mol) and 82.1 g (0.182 mol) of LAP-NMG from Example 3 are added, while stirring, and the mixture is heated to 40 to 50° C. for 1 hour. 1 l of a 10% strength clear, colorless, aqueous LAP-NMG hydrochloride solution is obtained with a pH of 5.5 to 6.5.

Example 6
Lauryl/myristylamidopropyl-N-methylglucamine lactate solution (LAP-NMG lactate solution)

1 l of a 10% strength clear, colorless, aqueous lactate solution having a pH of 6.5 to 7 is obtained in a manner corresponding to that described in Example 3 from 900 ml of water, 21.5 g (0.174 mol) of lactic acid and 78.5 g (0.174 mol) of LAP-NMG (from Example 3).

Example 7
Palmityl/stearylamidopropyl-N-methylglucamine hydrochloride (PAP-NMG.HCl) solution 1 l of a 10% strength solution of PAP-NMG.HCl is obtained with a pH of 5 in a corresponding manner from 900 ml of water, 16.2 g (0.164 mol) of concentrated hydrochloric acid and 83.8 g (0.164 mol) of palmityl/stearylamidopropyl-N-methylglucamine (from Example 4).

Example 8
Palmityl/stearylamidopropyl-N-methylglucamine lactate solution (PAP-NMG lactate solution)

1 l of a 10% strength lactate solution is obtained with a pH of 6.5 in a corresponding manner from 900 ml of water, 19.4 g (0.157 mol) of lactic acid and 80.6 g (0.157 mol) of palmityl/stearylamidopropyl-N-methylglucamine (from Example 4).

II. USE EXAMPLES
Possible uses of the products prepared are shown in the following examples:

Example A
Hair shampoo (formulation 1):
- 40.00% of sodium alkyl ether-sulfate
- 30.00% of LAP-NMG.HCl solution (10% strength, Example 5) or
  LAP-NMG lactate solution (10% strength, Example 6) or
  PAP-NMG.HCl solution (10% strength, Example 7) or
  PAP-NMG lactate solution (10% strength, Example 8)
- 0.30% of perfume oil
- 0.05% of preservative
- 28.65% of water
- about 1.00% of sodium chloride

Example B
Hair shampoo (formulation 2):
- 30.00% of sodium alkyl ether-sulfate
- 20.00% of LAP-NMG.HCl solution (10% strength, Example 5) or
  LAP-NMG lactate solution (10% strength, Example 6) or
  PAP-NMG.HCl solution (10% strength, Example 7) or
  PAP-NMG lactate solution (10% strength, Example 8)
- 5.00% of sulfosuccinic acid ester
- 5.00% of alkylamidopropylbetaine
- 0.30% of perfume oil
- 0.05% of preservative
- 38.85% of water
- about 0.80% of sodium chloride

Example C
All-purpose cleaner:
- 12.00% of secondary alkanesulfonate
- 20.00% of LAP-NMG.HCl solution (10% strength, Example 5) or
  LAP-NMG lactate solution (10% strength, Example 6) or
  PAP-NMG.HCl solution (10% strength, Example 7) or
  PAP-NMG lactate solution (10% strength, Example 8)
- 0.20% of perfume oil
- 0.05% of preservative
- 67.75% of water

Example D
Manual dishwashing composition:
- 40.00% of secondary alkanesulfonate
- 21.40% of sodium alkylether-sulfate
- 20.00% of LAP-NMG.HCl solution (10% strength, Example 5) or
  LAP-NMG lactate solution (10% strength, Example 6) or
  PAP-NMG.HCl solution (10% strength, Example 7) or
  PAP-NMG lactate solution (10% strength, Example 8)
- 0.20% of perfume oil
- 0.05% of preservative
- 18.35% of water

Example E
Disinfectant cleaner:
- 10.00% of coconut alkyl-dimethylamine oxide
- 10.00% of alkyldimethylbenzylammonium chloride
- 20.00% of LAP-NMG.HCl solution (10% strength, Example 5) or
  LAP-NMG lactate solution (10% strength, Example 6) or
  PAP-NMG.HCl solution (10% strength, Example 7) or
  PAP-NMG lactate solution (10% strength, Example 8)
- 0.20% of perfume oil
- 0.05% of preservative
- to 100.00% of water
- Sodium hydroxide solution (10% strength): pH 10

Example F
Viscosity-increasing action:

A potent viscosity-increasing action is obtained in combination with the base surfactants usually used (for example sodium alkyl ether-sulfates), especially with LAP-NMG salts, cf. the following Table 2:

Table 2:

(Viscosity-increasing action by addition of the salts according to the invention to sodium alkyl ether-sulfate)

| % of sodium chloride | Sodium alkyl ether-sulfate, 15% of WAS*) | Sodium alkyl ether-sulfate: LAP-NMG lactate, Example 6 (7:3) 15% of WAS*) | Sodium alkyl ether-sulfate: LAP-NMG-HCl Example 5 (7:3) 15% of WAS*) |
| --- | --- | --- | --- |
| 1 |  | >50000 mPas (gel) | >50000 mPas (gel) |
| 2 | 260 mPas | >50000 mPas (gel) | >50000 mPas (gel) |
| 3 | 9200 mPas | 8800 mPas | 4700 mPas |
| 4 | 36000 mPas | 2800 mPas | 1800 mPas |
| 5 | 54000 mPas |  |  |

*)The abbreviation "WAS" means wash-active substance.

We claim:

1. An amidopropyl-N-alkyl-polyhydroxyalkylamine in an essentially isolated form of the following formula (1)

(1)

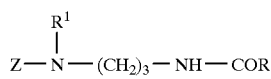

in which

Z is a linear polyhydroxyhydrocarbon radical having at least 2 free or oxyalkylated hydroxyl groups, $R^1$ is a $C_1$ to $C_7$-alkyl radical or $C_2$ to $C_4$-hydroxyalkyl radical and COR is an aliphatic acyl radical having 6 to 22 carbon atoms.

2. A polyhydroxyalkylamine as claimed in claim 1, in which, in formula (1),

Z is a polyhydroxyalkyl radical having 3 to 18 carbon atoms and 2 to 13 hydroxyl groups, $R^1$ is methyl, ethyl, propyl, isopropyl or —$CH_2CH_2OH$ and COR is a fatty acyl radical having 8 to 18 carbon atoms.

3. A polyhydroxyalkylamine as claimed in claim 1, in which, in formula (1),

Z is a radical of a sugar-alcohol which is derived from a reducing mono- or disaccharide, $R^1$ is methyl, ethyl, propyl or isopropyl and COR is a fatty acyl radical having 8 to 18 carbon atoms, derived from an acid selected from the group consisting of hydrogen halide acids, carbonic acid, phosphoric acid, sulfuric acid, $C_1$ to $C_3$-monocarboxylic acids, $C_{12}$ to $C_{18}$-monocarboxylic acids, dicarboxylic acids of the formula HOOC—$(CH_2)_n$—COOH, in which n is 0 or an integer from 1 to 8, fumaric acid, maleic acid, monohydroxy-monocarboxylic acids, monohydroxy-dicarboxylic acids, dihydroxy-dicarboxylic acids, monohydroxy-tricarboxylic acids, hydroxybenzoic acids and phthalic acids.

4. A polyhydroxyalkylamine as claimed in claim 3, in which Z is a sorbityl radical.

5. A polyhydroxyalkylamine as claimed in claim 1, in which, in formula (1), Z is a sorbityl radical, $R^1$ is methyl and COR is a fatty acyl radical having 8 to 18 carbon atoms, derived from an acid selected from the group consisting of hydrogen halide acids, carbonic acid, phosphoric acid, sulfuric acid, $C_1$ to $C_3$-monocarboxylic acids, lactic acid and the fruit acids.

6. A method for preparing a detergent and cleansing composition which comprises incorporating an amidopropyl-N-alkyl-polyhydroxyalkyl-amine as claimed in claim 1 by mixing into a detergent and cleansing composition.

7. A method for preparing a hair and body cleansing composition which comprises incorporating an amidopropyl-N-alkyl-polyhydroxyalkyl-amine as claimed in claim 1 by mixing into a detergent and cleaning composition.

8. A process for the preparation of an amidopropyl-N-alkyl-polyhydroxyalkylamine of the following formula (1)

(1)

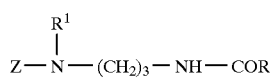

in which

Z is a linear polyhydroxyhydrocarbon radical having at least 2 free or oxyalkylated hydroxyl groups, $R^1$ is a $C_1$ to $C_7$-alkyl radical or $C_2$ to $C_4$-hydroxyalkyl radical and COR is an aliphatic acyl radical having 6 to 22 carbon atoms, which comprises a) reaction of a compound of the formula (2)

(2)

in which Z and $R^1$ have the meanings given, with acrylonitrile ($CH_2$=CH—CN) in a polar solvent at a temperature of 50 to 100° C. to form a compound of the formula (3)

in which Z and $R_1$ have the meanings given, (3)

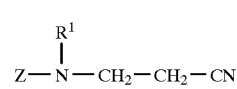

(b) reaction of the product obtained in step a) with hydrogen in the presence of ammonia and a hydrogenation catalyst at a temperature of 20 to 80° C. under a hydrogen pressure of 10 to 80 bar, to form a compound of the formula (4)

(4)

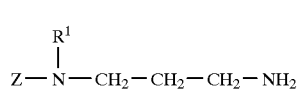

in which Z and $R^1$ have the meanings given, and (c) monoacylation of the product obtained in step b) with an acid or acid derivative derived from the acyl radical COR in formula (1) in the melt in the presence of an alkaline catalyst at a temperature of 80 to 130° C. to form a compound of the formula (1) mentioned.

9. The process as claimed in claim 8, which comprises a) reaction of a compound of the formula (2) with acrylonitrile in a molar ratio of about 1:1 in methanol, ethanol, propanol or isopropanol as the solvent at a temperature of 50 to 100° C., b) reaction of the product obtained in step a) with hydrogen in the presence of 1 to 10 mol of ammonia per mole of nitrile compound of the formula (3) and of Raney nickel as the hydrogenation catalyst at a temperature of 20 to 80° C. under a hydrogen pressure of 10 to 80 bar and c) monoacylation of the product obtained in step b) in the melt with a fatty acid $C_1$ to $C_4$-alkyl ester derived from the acyl radical COR in formula (1) in the presence of an alkali metal hydroxide or an alkali metal $C_1$ to $C_4$-alcoholate as the catalyst at a temperature of 80 to 130° C.

10. The process as claimed in claim 8, which comprises a) reaction of a compound of the formula (2) with acrylonitrile in a molar ratio of about 1:1 in methanol as the solvent at a temperature of 60 to 90° C., b) reaction of the product obtained in step a) with hydrogen in the presence of 3 to 6 mol of ammonia per mole of nitrile compound of the formula (3) and of Raney nickel as the hydrogenation catalyst at a temperature of 30 to 60° C. under a hydrogen pressure of 30 to 60 bar and c) monoacylation of the product obtained in step b) in the melt with a fatty acid methyl ester derived from the acyl radical COR in formula (1) in the presence of an alkali metal hydroxide or an alkali metal methylate as the catalyst at a temperature of 90 to 120° C.

11. A compound obtained by (a) reacting a compound of the formula (1)

(1)

in which

Z is a linear polyhydroxyhydrocarbon radical having at least 2 free or oxyalkylated hydroxyl groups, and $R^1$ is a $C_1$ to $C_7$-alkyl radical or $C_2$ to $C_4$-hydroxyalkyl radical with acrylonitrile in a polar solvent at a temperature of 50 to 100° C. to form a compound of the formula (2)

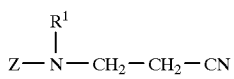

(2)

(b) reacting the product obtained in step (a) with hydrogen in the presence of ammonia and a hydrogenation catalyst at a temperature of 20 to 80° C. under a hydrogen pressure of 10 to 80 bar, to form a compound of the formula (3)

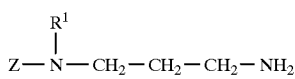

(3)

in which Z and $R^1$ having the meaning given, and (c) monoacylation of the product obtained in step (b) with an acid or acid derivative having 6 to 22 carbon atoms in the melt in the presence of an alkaline catalyst at a temperature of 80 to 130° C.

12. A compound as claimed in claim 11, obtained by (a) reacting a compound of the formula (1) with acrylonitrile in a molar ratio of about 1:1 in methanol, ethanol, propanol or isopropanol as the solvent at a temperature of 50 to 100° C., (b) reacting the product obtained in step (a) with hydrogen in the presence of 1 to 10 mol of ammonia per mole of nitrile compound of the formula (2) and of Raney nickel as the hydrogenation catalyst at a temperature of 20 to 80° C. under a hydrogen pressure of 10 to 80 bar and (c) monoacylation of the product obtained in step (b) in the melt with a fatty acid $C_1$ to $C_4$-alkyl ester in the presence of an alkali metal hydroxide or an alkali metal $C_1$ to $C_4$ alcoholate as the catalyst at a temperature of 80 to 130° C.

13. A compound as claimed in claim 11, obtained by (a) reacting a compound of the formula (1) with acrylonitrile in a molar ratio of about 1:1 in methanol as the solvent at a temperature of 60 to 90° C., (b) reacting the product obtained in step (a) with hydrogen in the presence of 3 to 6 mol of ammonia per mole of nitrile compound of the formula (2) and of Raney nickel as the hydrogenation catalyst at a temperature of 30 to 60° C. under a hydrogen pressure of 30 to 60 bar and (c) monoacylation of the product obtained in step (b) in the melt with a fatty acid methyl ester in the presence of an alkali metal hydroxide or an alkali metal methylate as the catalyst at a temperature of 90 to 120° C.

14. A compound as claimed in claim 13, obtained from a compound of formula (1) wherein Z is a polyhydroxyalkyl radical having 3 to 18 carbon atoms and 2 to 13 hydroxyl groups, and $R^1$ is methyl, ethyl, propyl, isopropyl or —$CH_2CH_2OH$ and an acid or acid derivative having 8 to 18 carbon atoms.

15. A compound as claimed in claim 11 from an acid from the group consisting of hydrogen halide acids, carbonic acid, phosphoric acid, sulfuric acid, $C_1$ to $C_3$-monocarboxylic acids, $C_{12}$ to $C_{18}$-monocarboxylic acids, dicarboxylic acids of the formula HOOC—$(CH_2)_n$—COOH, in which n is 0 or an integer from 1 to 8, fumaric acid, maleic acid, monohydroxy-monocarboxylic acids, monohydroxy-dicarboxylic acids, dihydroxy-dicarboxylic acids, monohydroxy-tricarboxylic acids, hydroxy-benzoic acids and phthalic acids, obtained from a compound of formula (1) wherein Z is a radical of a sugar-alcohol which is derived from a reducing mono- or disaccharide and $R_1$ is methyl, ethyl, propyl or isopropyl and an acid or acid derivative having 8 to 18 carbon atoms.

16. A compound as claimed in claim 11 obtained from a compound of formula (1) in which Z is a sorbityl radical.

17. A compound as claimed in claim 11 from an acid from the group consisting of hydrogen halide acids, carbonic acid, phosphoric acid, sulfuric acid, $C_1$ to $C_3$-monocarboxylic acids, lactic acid and the fruit acids, obtained from a compound of formula (1) in which Z is a sorbityl radical and $R^1$ is methyl and from monoacylation with an acid on acid derivative having 8 to 18 carbon atoms.

* * * * *